Figure 1:
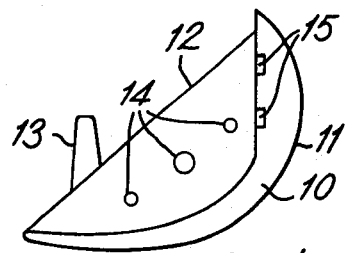

United States Patent [19]
Lee et al.

[11] 3,958,278
[45] May 25, 1976

[54] ENDOPROSTHETIC KNEE JOINT
[75] Inventors: Alan John Clive Lee, Exeter; Robin Sydney Mackwood Ling, Teignmouth, both of England
[73] Assignee: National Research Development Corporation, London, England
[22] Filed: Apr. 22, 1975
[21] Appl. No.: 570,954

[30] Foreign Application Priority Data
Apr. 22, 1974 United Kingdom............... 17502/74

[52] U.S. Cl................................. 3/1.911; 128/92 C
[51] Int. Cl.² ........................................... A61F 1/24
[58] Field of Search .......................... 3/1, 1.9–1.913; 128/92 C, 92 CA

[56] References Cited
UNITED STATES PATENTS
3,824,630   7/1974   Johnston.............................. 3/1.911
3,852,830   12/1974  Marmor...................................... 3/1
3,868,730   3/1975   Kaufer et al................................ 3/1
3,869,731   3/1975   Waugh et al............................... 3/1

Primary Examiner—Ronald L. Frinks
Attorney, Agent, or Firm—Cushman, Darby & Cushman

[57] ABSTRACT

An endoprosthetic knee joint device is suited to a unicondylar procedure in which only one compartment of the knee is treated, or a duocondylar procedure, the latter employing a pair of like femoral components and a tibial component having a common platform defining separate recesses for similar pads. In addition the device maximizes the use of advantageous material properties, allows pad replacement in the event of wear, and allows pad thickness selection to correct for varus and valgus deformities.

11 Claims, 8 Drawing Figures

ENDOPROSTHETIC KNEE JOINT

This invention concerns endoprosthetic devices and more particularly such devices for replacing the articulatory function of the knee joint.

Commercially available endoprosthetic knee joint devices have, until recently, conventionally involved a mechanically linked hinge structure comprising separate femoral and tibial components and a coupling pin which co-operates with each of the former components in bearing engagement to provide articulation by rotation of the components about the longitudinal axis of the pin. However, while such devices have been used beneficially, they are subject to disadvantages which include the transmission of forces through the hinge structure which forces tend to weaken the securement of the femoral and tibial components to the femur and tibia. This particular disadvantage arises notwithstanding the common practice of an all-metal construction of the hinge with deep bone penetration for purposes of securement.

Recently, proposals have been made for devices comprising separate femoral and tibial components which co-operate in direct mutually articulatory bearing engagement while being held in such engagement by indirect coupling through the muscular and ligamentous components of the natural joint capsule. These proposals have involved the use of femoral and tibial components which are wholly of integral metal and plastics material construction, respectively, to take advantage, inter alia, of the improved frictional properties available with such a combination of materials as compared to that between two metal components. However, in so far as plastics material does not normally have similar mechanical stability and strength to metal, these recent proposals may be subject to long term disadvantage. For example, the relevant devices are normally employed in respect of arthritic conditions when the bone quality is poor and it is possible that the stability of the tibial component securement will degenerate unless these components are bulky and deeply penetrating, which latter requirements are themselves disadvantageous. Also, it is possible as a result of the greater freedom of motion afforded in these more recent devices, that the tibial components will be subjected to wear such that replacement becomes necessary.

An object of the present invention is to reduce these possible disadvantages and, to this end, the invention provides an endoprosthetic knee joint device comprising: a femoral component defining an elongate longitudinally-convexly-curved first bearing surface, adapted for securement to the femur to locate said first surface as a femoral condylar surface replacement, and of integral construction from a first material; and a tibial component of multi-part construction including a base part and a bearing part respectively made of said first material and a second material, said bearing part defining a substantially flat or concavely-dished second bearing surface for mutual articulatory engagement with said first surface, said base part and bearing part being adapted for releasable captive engagement of the latter in the former, said base part being adapted for securement to the tibia to locate said second surface as a tibial condylar surface replacement, and said first material being of greater mechanical stability and strength than said second material.

Normally the first and second materials will be metal and plastics material, respectively.

The benefits of the presently proposed device are that the tibial component base part can more readily provide a rigid and stable support for the associated bearing part compared to an integral plastics component, while at the same time the frictional advantages of the metal femoral/plastics tibial engagement can be obtained, and the tibial component can be replaced without such extensive surgery as would otherwise be the case. A further benefit is that a relatively standardized tibial component securement is possible with a given form of base part, while different bearing parts can be used therewith to take account of conditions such as varus and valgus deformisies wh are individual to patients.

Figure 2:
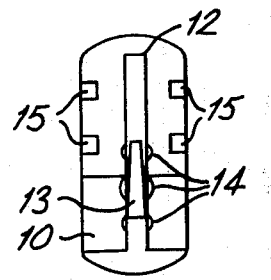
Figure 3:
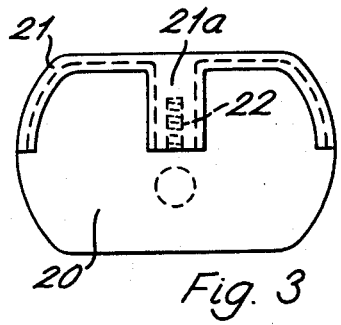
Figure 6:
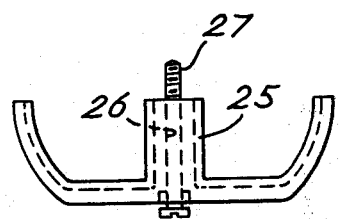
Figure 4:
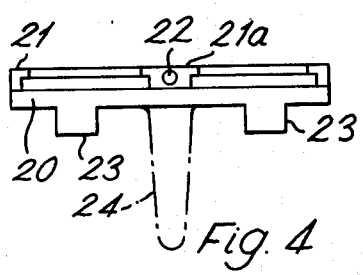
Figure 5:
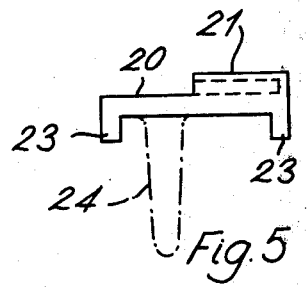
Figure 7:
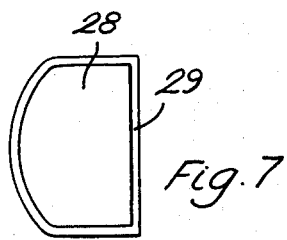
Figure 8:
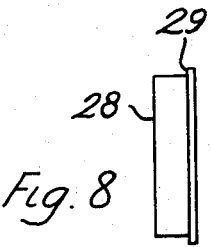

For a fuller understanding of the invention, one embodiment of the same will now be described, by way of example, with reference to the accompanying drawings in which:

FIGS. 1 and 2 respectively illustrate in side and end views the form of femoral component of the relevant embodiment, FIGS. 3, 4 and 5 respectively illustrate in plan, side and end views one part of the associated tibial component, FIG. 6 illustrates another such tibial component part in plan view, and FIGS. 7 and 8 respectively illustrate in plan and side views yet another tibial component part of the same embodiment.

The embodiment illustrated by the drawings will comprise two like femoral components as illustrated by FIGS. 1 and 2. These components are associated with a single tibial component of multiconstruction form including a base part formed by a major support member as in FIGS. 3 to 5 and a locking member as in FIG. 6, and two like bearing parts as illustrated in FIGS. 7 and 8, the latter parts being releasably held in the support member by the locking member for respective engagement with the femoral components.

The illustrated form of femoral component comprises a generally arcuate strip bearing member 10 of which the convex face 11 defines a bearing surface. This surface has a smooth longitudinal curvature which is preferably of a higher value over one end portion than the other end portion to simulate the sagittal curvature of a femoral condyle. Conveniently, this longitudinal curvature is derived from a succession of two circular arcs having a common tangent at their junction. The face 11 is also convexly curved in its transverse direction to simulate the lateral curvature of a femoral condyle. Again, this transverse curvature is conveniently circular arcuate.

The femoral component is adapted remotely from the face 11 for securement to a femoral condyle with the use of a gap-filling medium such as a suitable acrylic cement. In this instance, such adaptation comprises the provision of a rib 12 extending from the rear of the member 10 in the longitudinal medial plane thereof, the rib being in the form of a chord of member 10. Additional features of this adaptation are provision of a short tapered stem 13 extending from the free outermost edge of the rib 12 adjacent the end portion of the member 11 of lesser curvature; the provision of dimples 14 on the side faces of the rib 12; and the provision of notches 15 in the rear face of the member 11 at its end portion of greater curvature, the latter portion being thickened over part of its length to receive such notches.

The illustrated major support member comprises a platform 20 of substantially uniform thickness, having parallel major sides and rounded minor sides. One major face of the platform has a side wall 21 upstanding therefrom at its periphery, which wall extends partway around one minor side, continues along one major side, and then partway around the other minor side of the platform. This wall also has an extension 21a from its central region partway across the platform 20 so that the wall forms an E-shape in plan view. An additional feature of the wall 21 is that its inner edges relative to the platform 20 are undercut except that at the free end of extension 21a, the latter edge portion being bored and threaded at 22.

The other major face of the platform is adapted for securement to the tibia with the use of gap-filling medium by the provision of four lugs 23 which depend from respective locations adjacent the ends of the major sides of the platform. An additional feature of fixation adaption may be the provision of an intramedullary stem 24 shown in broken outline projecting from the central region of the relevant face of the platform 20. This addition will normally be appropriate only in circumstances where a gap-filling medium is not used for securement.

The illustrated locking member is denoted at 25 and comprises an E-shaped member similar to the side wall 21 and its extension 21a, the member 25 being shaped and dimensioned to seat on the platform 20 and complete the side wall therearound and wall extension thereacross. For this purpose the member 25 is appropriately bored at 26 and associated with a screw 27 to pass through the bore 26 and engage the bore 22. The member 25 is also undercut in similar manner to the side wall 21/extension 21a so that, when the member 25 is located on the platform, there are formed two similar recesses in the resultant overall support platform which recesses have undercut sides wholly therearound. In this instance these recesses are each of like D-shape but of reflected geometry with their curved edges outermost in back-to-back spaced disposition.

The illustrated bearing part is denoted 28, it is of flat plate form with the D-shape just mentioned, it has a flanged edge profile 29 complementary to that of the above-mentioned undercut formations, and it has a thickness greater than the depth of the recesses of the support platform.

In use of the illustrated parts, each femoral condyle is appropriately prepared with slotting to receive a separate femoral component. These components will be located in substantially parallel manner with their bearing surfaces exposed and conforming to the geometry of the condylar surfaces which they replace. The tibia is prepared with sectioning and boring to receive the correspondingly adapted major face of the support member platform 20, the platform being located with its side wall in the medial, posterior and lateral aspects. Two bearing parts 28 are then respectively anteriorly engaged in the spaces between the side wall 21 and extension 21a, and these parts are retained by location of the locking member 25 around the remaining exposed edges of the bearing parts and securing with the screw 27. Following surgical closure the femoral components and tibial bearing parts respectively engage in mutual articulatory manner.

In the construction of the illustrated embodiment the allocation of materials as indicated above is followed, namely, metal for the femoral components and tibial support parts, and plastics material for the tibial bearing parts.

While the invention has been described with more particular reference to the illustrated embodiment, it is not intended to be limited thereto. Indeed, the embodiment in question can form one of a family of devices suited to application in different circumstances. For example, although the embodiment comprises two separate unicondylar femoral components and a unitary bicondylar component, a modified device can employ the same femoral components and two separate unicondylar tibial components which are similar and effectively formed by separation of the illustrated unitary support assembly into two lateral parts. Such a modified device is appropriate to retention of the cruciate ligaments and simplification of surgery by the possibility of adequate access without patella detachment. Also, single components of such a device are appropriate to a unicondylar replacement.

Cruciate retention can also be effected with a different modification in which the unitary tibial support assembly is not completely separated, but slotted through the extension 21a. A similar modification can also be made to the femoral components so that these are integrated to a unitary slotted form.

Modification can also be effected in other respects. For example, the tibial bearing parts preferably each have a flat bearing surface. This reduces the constraints which may otherwise arise in respect of relative femoral-tibial component location, and those of the degrees and ranges of mutual articulation. However, it may be appropriate for some circumstances to provide a concavity in the tibial bearing surfaces to enhance lateral stability.

Also, as has been intimated in the above description, the adaption of the components for the purposes of securement can be modified, although the general preference is for relatively low relief configurations for association with gap-filling medium.

We claim:
1. An endoprosthetic knee joint device comprising:
a femoral component defining an elongate longitudinally-convexly-curved first bearing surface, adapted for securement to the femur to locate said first surface as a femoral condylar surface replacement, and of integral construction from a first material;
a tibial component base part made of said first material, having a platform portion defining in one major face thereof a recess with undercut side walls, having a clamp member which forms part of said recess and said side walls and is detachable to allow access to said recess, and said platform portion being adapted remotely from said recess for securement to the tibia as a tibial condylar replacement;
and a tibial component bearing part made of a second material of lesser mechanical stability and strength than said first material, being substantially complementary to but having a thickness greater than the depth of said recess, being releasably captively engaged in said recess by said side walls and said clamp member, and defining remotely from said recess a second bearing surface in mutual articulatory engagement with said first bearing surface.

2. A device according to claim 1 wherein said first and second materials are respectively metal and plastics materials.

3. A device according to claim 1 wherein said second bearing surface is flat.

4. A device according to claim 1, wherein said femoral component comprises a strip form member of which one major face defines said first surface, and the securement adaptation includes a rib extending along the other major face of said strip member in the manner of a chord relative to said first surface.

5. A device according to claim 4 wherein said first surface has greater longitudinal curvature over one end portion thereof than the other such portion, and the securement adaptation further includes a stem projecting from the free edge of said rib adjacent said other portion.

6. A device according to claim 5 wherein the longitudinal curvature of said first surface is defined by a succession of two circular arcs having a common tangent at their junction.

7. A device according to claim 4, wherein the side faces of said rib are dimpled.

8. A device according to claim 4, wherein said strip member is thickened over one end portion thereof and notched, remotely from said first surface, in the thickened area.

9. A device according to claim 1 comprising a pair of like femoral components each as aforesaid, and a tibial component comprising a common base part and two similar bearing parts as aforesaid, said bearing parts being engageable in said common base part together but in mutually spaced manner.

10. A device according to claim 1 comprising:
a pair of like femoral components each as aforesaid;
and a pair of like tibial component bearing parts each as aforesaid, and wherein said base part includes said platform portion having, in plan view, an E-shaped side wall with undercut inwardly facing edges, and said clamp member is of similar undercut E-shape detachably connected to said platform portion to continue said side wall and define two D-shaped recesses in back-to-back spaced disposition.

11. A device according to claim 1 wherein said second bearing surface is concavely dished.

* * * * *